United States Patent [19]
Hausman

[11] Patent Number: 5,676,667
[45] Date of Patent: Oct. 14, 1997

[54] BONE FIXATION APPARATUS AND METHOD

[76] Inventor: Michael Hausman, 168 E. 95th St., New York, N.Y. 10128

[21] Appl. No.: 569,694

[22] Filed: Dec. 8, 1995

[51] Int. Cl.⁶ .................................................. A61B 17/58
[52] U.S. Cl. ................................ 606/69; 606/73; 606/59
[58] Field of Search .................................. 606/59, 69, 70, 606/71, 54, 57, 74, 61

[56] References Cited

U.S. PATENT DOCUMENTS

| | | | |
|---|---|---|---|
| 1,025,008 | 4/1912 | Miner . | |
| 2,406,832 | 3/1946 | Hardinge | 128/87 |
| 2,414,882 | 1/1947 | Longfellow | 128/92 |
| 2,526,959 | 10/1950 | Lorenzo | 128/92 |
| 3,528,085 | 9/1970 | Reynolds, Jr. | 128/92 |
| 4,388,921 | 6/1983 | Sutter et al. | 128/92 |
| 4,403,607 | 9/1983 | Woo et al. | 128/92 |
| 4,793,335 | 12/1988 | Frey et al. | 128/92 |
| 4,794,918 | 1/1989 | Wolter | 128/92 |
| 4,936,844 | 6/1990 | Chandler et al. | 606/69 |
| 5,433,719 | 7/1995 | Pennig | 606/73 |
| 5,527,311 | 6/1996 | Procter et al. | 606/61 |

OTHER PUBLICATIONS

The Journal of Bone and Joint Surgery, "May Anatomical Bone Plates", Mar. 1990.

*Primary Examiner*—Michael Buiz
*Assistant Examiner*—David O. Reip
*Attorney, Agent, or Firm*—Sofer & Haroun, LLP

[57] ABSTRACT

A fixation plate for fixing the position of a fractured bone is provided. The fixation plate includes an elongated rigid plate having a plurality of first apertures spaced along the length of the plate. The first apertures are arranged and sized to receive threaded fasteners for fastening the plate to the bone on both sides of the fracture. The fixation plate also includes a plurality of second apertures spaced along the length of the plate. The second apertures, which are smaller than the first apertures, are arranged and sized to receive tacks to temporarily attach the plate to the bone on both sides of the fracture.

24 Claims, 3 Drawing Sheets

BONE FIXATION APPARATUS AND METHOD

FIELD OF THE INVENTION

This invention relates to an internal bone fixation apparatus and method, and particularly to an improved bone fixation plate and stabilization pins and a method for reconstructing bone fractures using this fixation system.

BACKGROUND OF THE INVENTION

Clinical studies have long established that under appropriate conditions, the internal fixation of fractures of bones of the human body with sturdy metal plates is effective in promoting fracture healing. Accordingly, bone fixation plates are well accepted for bracing bone segments of fractured bones.

Bone fixation plates are typically constructed of a suitable reasonably rigid metal, such as stainless steel or titanium alloy. Plates constructed from graphite material, methyl methacrylate or polyglycolic acid compounds may also be utilized. These fixation plates are usually somewhat arcuate and may be bent into a shape that conforms to the surface of the bone to which it is attached. In this way, the plate may closely fit the outside curvature of human bones. The fixation plate also includes openings or apertures through which attachment screws fixedly mount the plate to the bone segments. Typically, the apertures are countersunk so that the heads of the screws are flush with the plate and therefore nest in the countersunk apertures of the fixation plate.

Attachment of a fixation plate to a patient's bone is accomplished by reducing or positioning the fracture fragments and maintaining a fixed position while the plate is fixed to the bone using specially designed bone clamps. In this context, reducing or reduction refers to the procedure where two or more bone fragments are brought back into their normal positions. This requires circumferential dissection of at least some portions of the bone to accommodate such specially designed bone clamps. However, the use of these clamps in a manner described above may lead to a loss of reduction or displacement of the intended position of the fracture or the plate. Furthermore, the clamps may sometimes interfere with the optimal placement of the plate. In some circumstances, the bone plate may be initially fastened to each of the bone segments with screws placed in holes drilled into the bone.

In certain situations where a patient is suffering from comminuted fractures comprising multiple bone fragments, the above described technique may lead to problems. For example, during the operation, X-rays may be necessary to confirm an adequate reduction and satisfactory positioning of the fracture. If the surgeon determines that further adjustments are necessary, the clamps or screws which have been placed to secure the plate must be removed. Accordingly, it is common that some of the bone clamps or screws are removed, including those clamping the fixation plate in position in order to check the position of the plate and bone segments and make slight adjustments.

In this event, the screws fastening the plate to the bone segments are loosened or removed, and the plate is repositioned and refastened with screws to the bone segment. This procedure is repeated until position of the plate and the bone segments are satisfactory.

Repositioning of the plate in accordance with the above-described method may cause loss of reduction or require additional stripping of the bone and compromise of the blood supply. Furthermore, if screws are used to hold the plate to the bone, repositioning may require removal and replacement of the screws in new holes. This repositioning further weakens the bone and may compromise the screw fixation. Holes that are close to each other, may coalesce into a larger caliber hole and prevent a firm purchase of the screw. This may lead to suboptimal positioning of the bone and hardware or compromised and weakened fixation.

Accordingly, there is a need for a bone fixation apparatus and method that secures metal plates to fractured bones without the drawbacks mentioned above.

OBJECTS AND SUMMARY OF THE INVENTION

It is an object of the invention to provide a fixation system wherein a fixation plate may be temporarily affixed to a patient's fractured bone so that both the plate and the bone may be repositioned to the surgeon's satisfaction.

Another object of the invention is to prevent periosteal stripping of the bone and to facilitate piece-by-piece rebuilding of complex, comminuted fractures.

Another object of the invention is to provide a fixation system which substantially facilitates repositioning of the fixation plate and furthermore substantially eliminates unnecessary screw holes.

A further object of the invention is to provide a bone fixation plate having an array of first apertures for receiving screws to fasten the plate to the bone fragments of the fractured bone and an array of second apertures for receiving fixation pins for temporarily securing the plate to the bone.

The present invention is directed to an internal fixation plate and fixation pins. The fixation plates are provided with a first array of apertures for receiving screws to fasten the plate to the bone segments of a fractured bone. The fixation plates are also provided with a second array of additional apertures for receiving bone tacks, or screws, or pins, or the like, having a smaller diameter than the screws used with the first array of apertures. The fixation plate is attached to the fractured bone segments by placing the plate on the exposed surface of the fracture and temporarily securing it to the bone with pins, which may be threaded and beveled, to compress the plate and bone. The fracture may thus be assembled in a piece-by-piece fashion and X-rays may then be obtained. The plate and bone fragments may be individually adjusted as needed without having to disrupt the entire assembly. The pins may be selectively removed and replaced to permit repositioning of the bone fragments and/or plate until the proper position is obtained. The pins are configured such that they may be repositioned repeatedly without compromising the integrity of the bone and the placement of larger screws. The larger screws may be then placed to permanently secure the plate and bone.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION OF THE PRESENTLY PREFERRED EMBODIMENTS

Figure 4:
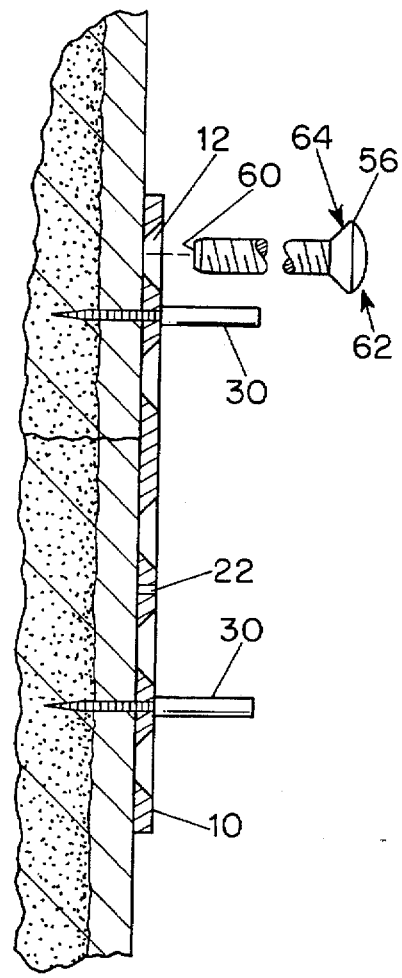
FIG. 4 is a sectional view taken along section A—A of FIG. 3 of the fixation plate attached to the bone by the wire tacks.

As shown in FIGS. 1A–1H, various forms of fixation plates 10 are illustrated in accordance with the presently preferred embodiment of the invention. Fixation plate 10 is formed preferably as a rigid plate, such as a metal plate constructed of stainless steel or titanium alloy. However, the fixation plate may be fabricated out of a graphite material, methyl methacrylate, resin, or bioabsorbable polyglycolic acid, and therefore the invention is not limited in scope in this respect. An array of apertures 12 for receiving shanks 60 of respective threaded fasteners, such as bone screws 56 (FIG. 4) are provided in the fixation plate. Preferably, apertures 12 are provided with countersunk regions 14 to receive heads 62 of bone screws 56. Underside 64 of head 62 corresponds with the countersunk regions 14 so that screws 56 nest within the fixation plate 10 (FIG. 4).

Depending on the particular application of fixation plate 10, the fixation plate is provided with a width between about 0.35 and 0.40 inches, and a thickness between about 0.04 and 0.20 inches. However, the invention is not limited in scope to such dimensions, and other plate dimensions may be used for appropriate applications. The length of the plate depends on the ultimate use for which the plate is intended and may be between about 1.4 and 10.0 inches. As well, the number of apertures 12 that are provided depends on the length of plate 10. For example, the number of apertures may vary between three apertures for a typically short plate and sixteen apertures for a typically long plate, although the invention is not limited in scope in this respect.

Figure 1A:
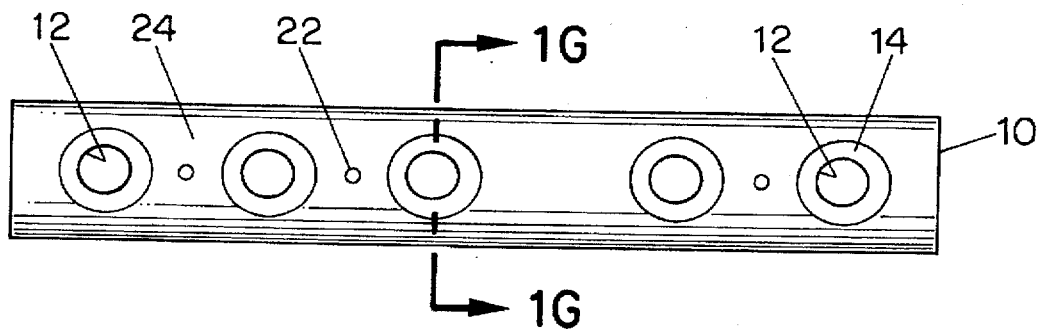
FIGS. 1A–1D illustrate plan views of bone fixation plates in accordance with the presently preferred embodiment of the invention.

In the embodiment illustrated in FIG. 1A, apertures 12 are arranged in a row or array centered along the length of plate 10, although the invention is not limited in scope to such an arrangement. FIG. 1A illustrates apertures 12 with an oval shape having a length (along the length of plate 10) slightly larger than their width (across the width of plate 10). However, the invention is not limited in scope in this respect and apertures with various shapes may be employed. For apertures with an oval shape, minor adjustments of the plate may be facilitated after attachment to the screws. The length of apertures may typically range between about 0.190 and 0.420 inches and the width of apertures may typically range between about 0.160 and 0.270 inches, for the majority of applications.

Figure 1B:
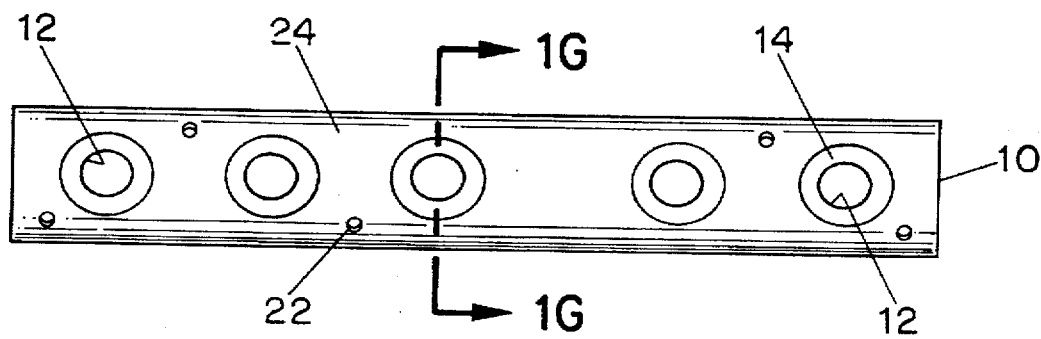
Figure 1C:
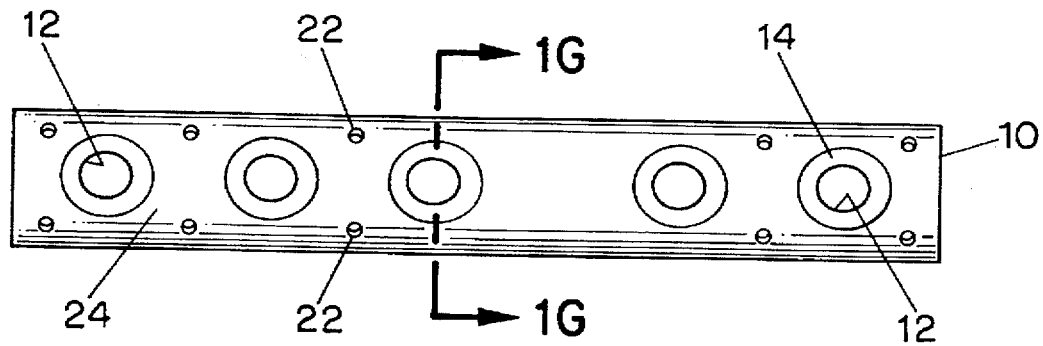
Figure 1D:
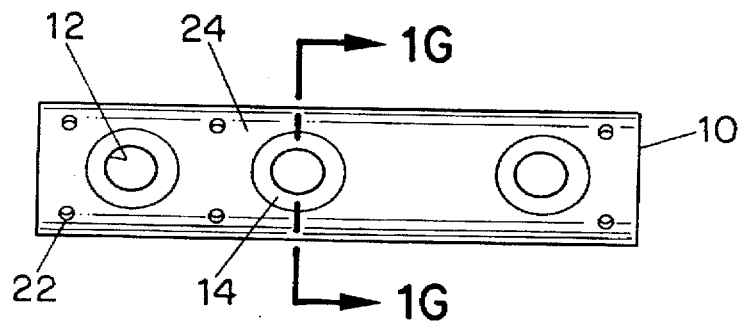
Figure 1E:
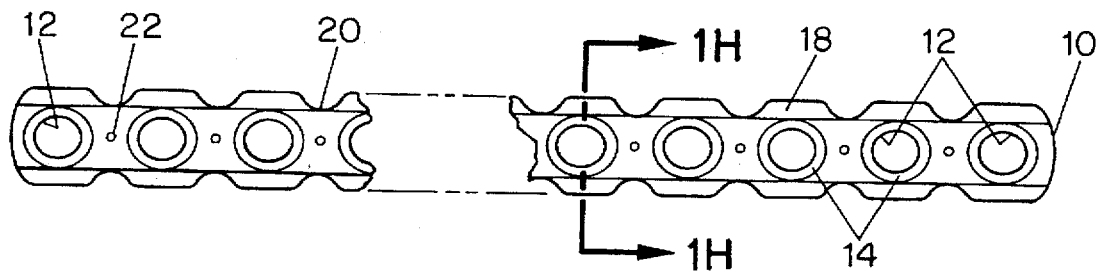
FIGS. 1E and 1F illustrate plan views of a bone fixation plate in accordance with a further embodiment of the invention.
Figure 1F:
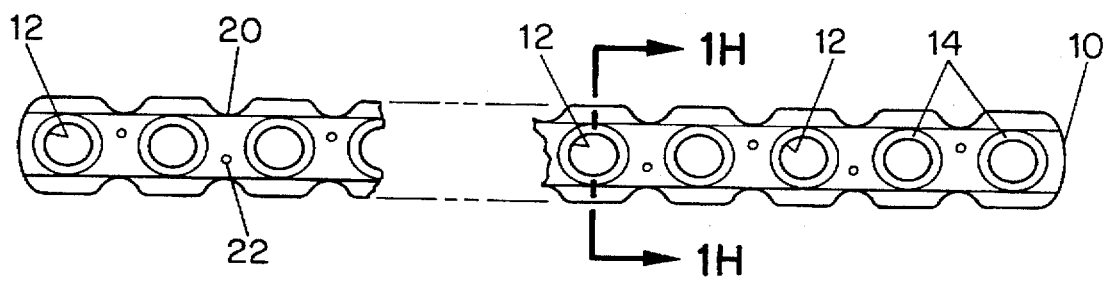
Figure 1G:
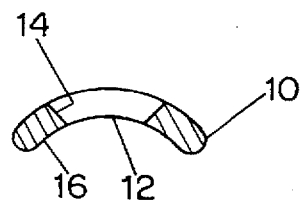
FIG. 1G is a sectional view taken along section A—A of FIGS. 1A–1D of the presently preferred embodiment of the bone fixation plate.
Figure 1H:
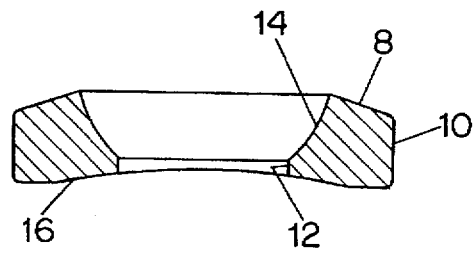
FIG. 1H is a sectional view taken along section A—A of FIGS. 1E and 1F.

Referring to FIGS. 1G and 1H, surface 16 of plate 10 is a concave surface to conform to the curve of the bone surface. For example, the plate illustrated in FIGS. 1A–1D and 1G may form an arch about 100 degrees for use with smaller bones such as metacarpal, whereas the plates shown in FIGS. 1E, 1F and 1H may have less of an arch for use with larger bones such as the ulna or tibia. The size (length, width and thickness) of plate 10 may depend at least upon its ultimate purpose, as the size will be greater for larger bones than for smaller ones.

As shown in FIG. 1H, the plate shown in FIGS. 1E and 1F may employ chamfer surfaces 18 to form a smooth transition from the screw head to the edge of the plate. Additionally, as shown in FIGS. 1E and 1F, sections of reduced width 20 may be provided in order to concentrate bending of the plate at section 20, and away from screw apertures 12.

Figure 2A:
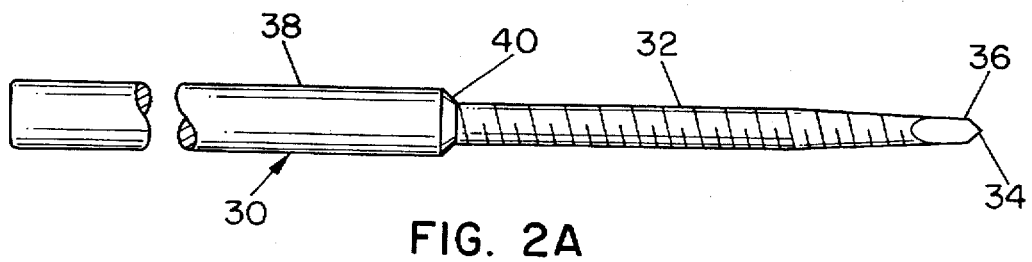
FIGS. 2A and 2B are side views, taken 90 degrees from each other, of the wire tack used with the fixation plates of FIGS. 1A–1H.
Figure 2B:
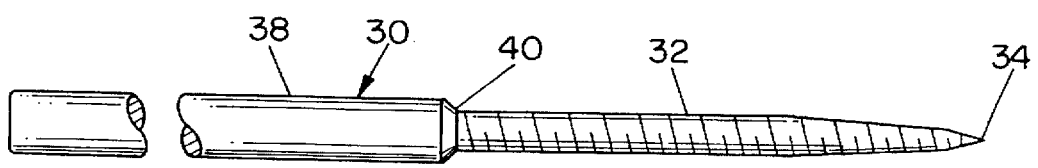

Each of the plates shown in FIGS. 1A–1H include an array of tack apertures 22, each having a diameter of about 0.06 inches, to accommodate tacks 30 shown in FIGS. 2A and 2B. The particular configuration for these tack apertures is such as to optimally and temporarily position plate 10 to the bone segments to which it is to be attached. Referring to FIGS. 1A and 1E, apertures 22 may be disposed in an array centered along the length of the plate. In an alternative embodiment, as illustrated in FIGS. 1B and 1C, apertures 22 may be staggered at the edges or positioned along the length at the edges of the plate. While the particular configuration of the array of tack apertures 22 is not important, it is preferred that the arrangement be such as to permit fastening of the plate by tacks through such tack apertures. It is also preferred that the tack apertures be positioned approximately evenly between apertures 12 along the length of the plate. If desired, a region 24 on each plate (FIGS. 1A–1D) may be left void of any apertures to permit inclusion of the part identification.

Referring to FIGS. 2A and 2B, a wire tack or needle 30 in accordance with a preferred embodiment of the present invention is shown. Tack 30 is provided with a threaded portion 32 which is tapered towards its sharp needle point 34 forming chisel edge 36. Threaded portion 32 of tack 30 forms threads having a major diameter of about 0.05 inches and a minor diameter of about 0.03 inches and may conveniently have 56 threads per inch, thereby providing good gripping of the bone material to which it is to be attached. Tack 32 is also provided with a chisel section 36 and needle point 34 to facilitate entry of the tack into the bone. As well, tack 32 is provided with a handle 38 which has a diameter of about 0.8 inches, forming a tapering portion 40 between the handle 38 and the threaded portion. The threaded portion of the needle has a length of between about 0.4 and 0.8 inches (depending on intended use), and the handle has a length of approximately 3.35 inches. However, the invention is not limited in scope to the particular shape or dimensions discussed above.

Figure 3:
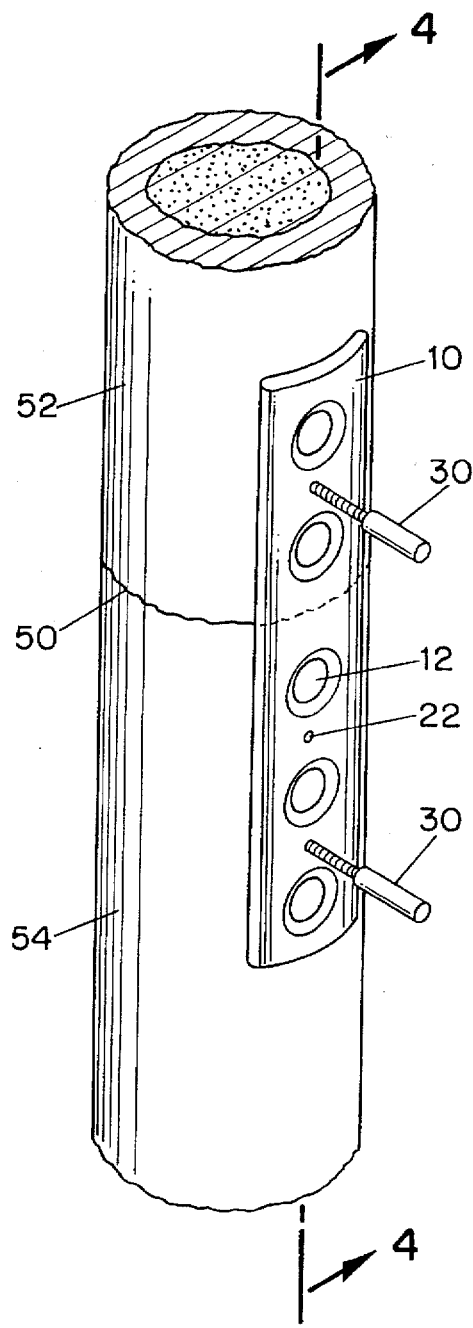
FIG. 3 is a perspective view of the fixation plate of FIG. 1A shown attached by the wire tack shown in FIGS. 2A and 2B to two segments of a bone.

Referring to FIGS. 3 and 4, the use of the fixation plate and pins is explained. For purposes of explanation, a fractured bone, which is somewhat cylindrical in shape, has a diaphyseal fracture 50 separating the bone into bone segments 52 and 54. It should be understood that although two bone segments are shown in FIG. 3 there are many other circumstances where a fractured bone contains more than two bone segments. In such circumstances more than two bone segments may be joined together by one or more plates, as will be explained in more detail.

Fixation plate 10 is to be mounted to the bone across the fracture. The bone segments and plate 10 are positioned across the fracture. The bone segments and plate may be clamped into position or the bone clamps may be omitted with the plate being attached to the bone segments using only the tacks. In either case, threaded portions 32 of tacks 30 are inserted into selected apertures 22 of plate 10 on each side of the fracture. The chisel edges 36 engage the bone surface to permit the tacks to be threaded into the bone segments on clockwise rotation of the tack. The tacks are threaded into the bone until surfaces 40 on the tacks seat into apertures 22 of plate 10 and bears against the plate to temporarily attach plate 10 against the bone surface. Hence, plate 10 is temporarily attached to the bone segments without the use of bone screws. If bone clamps are used to clamp the bone segments and plate, a number of the bone clamps may be removed as deemed appropriate to inspect the position of the bone segments and plate. If repositioning of the plate and or bone segments is required, repositioning is accomplished simply by removing selected tacks 30, and adjusting the position of the fixation plate and the bone segments with respect to each other, and reattaching the plate with tacks 30. Preferably, there are more apertures 22 than are necessary to temporarily attach the plate, so that upon repositioning the tacks may be assembled through different apertures 22, thereby assuring that tacks 30 bore into untapped bone material.

Bone screws 56 are threaded into the bone segments through apertures 22 to fasten plate 10 securely to the bone segments when the position of the bone segments and plate 10 are satisfactory. As shown in FIG. 4, the heads of screws 56 are arranged to be received in the recesses formed by counter-sunk regions 14. Conveniently, screws 56 may be self-tapping screws. Upon completion of the assembly of the plate to the bone segments with screws 56, wire tacks 30 are removed.

In the event of a comminuted fracture comprising multiple fragments of bone, the present invention permits sequential, fragment by fragment reduction and assembly of the fracture. A fixation plate, such as those illustrated in FIGS. 1A–1H is mounted to the first bone fragment of comminuted fracture. The first bone segment and the plate are attached together using the tacks illustrated in FIG. 2. A second bone segment is then placed near the first bone segment in order to substantially reduce the fragments. A second set of tacks such as those illustrated in FIG. 2 are then used to attach the plate to the second bone fragment. Thereafter, a third bone segment is placed near the second bone segment in order to substantially reduce the fragments. A third set of tacks, such as those illustrated in FIG. 2, are then used to attach the plate to the third bone fragment. This process continues until all bone fragments have been reduced. It will be appreciated that the above-described sequential reduction is an improvement to prior art procedures which comprise simultaneous reduction and fixation of all fragments and the plate with multiple bone clamps.

The present invention thus provides an effective technique for fastening fixation plates to bone segments without significantly damaging the bone. By temporarily attaching the fixation plate to the bone segments it is possible to substantially eliminate any damage to the bone at the regions where the screws are to fasten the plate to the bone, in accordance with the present invention. The plate and/or the bone segments may be repositioned to the satisfaction of the surgeon without damaging the regions where the screws will fasten the plate to the bone. Each screw fastening the fixation plate to the bone is fastened to the bone once, so the screws may be reliably set into the bone to secure the plate to the bone. The screws are not removed from or inserted to the bone during repositioning of the plate, thereby avoiding difficulties with weakened bone structure and poor securance of the fastening screws to the bone.

The fixation system according to the present invention may be used alone, or in combination with other fixation systems, such as fixation screws, Kirschner wires and/or intraosseous wire. If the bone is fractured into three or more segments, the fixation plate according to the present invention may be fastened to each of the bone segments, or to fewer than all segments, with reliance on other fixation techniques to fix the position of other segments, as well known in the art. In given circumstances it may be desirable to employ a plurality of fixation plates to fix the bone position.

It should be understood that the preferred embodiments and examples described are for illustrative purposes only and are not to be construed as limiting the scope of the present invention which is properly delineated only in the appended claims.

What is claimed is:

1. An elongated rigid fixation plate system for fixing the position of a fractured bone, said fixation plate system comprising:

a plurality of first apertures located along the length of said fixation plate, said first apertures receiving a threaded fastener at both sides of a fracture for fastening the plate to the bone, wherein said threaded fastener has a shaft of a first diameter and a head; and a plurality of second apertures smaller than said first apertures located along the length of said fixation plate, such that two or more of said second apertures removably receive a tack to temporarily and firmly attach said fixation plate to the bone at both sides of said fracture, wherein said tack has an insertion portion of a second diameter smaller than said first diameter of said threaded fastener.

2. The fixation plate of claim 1, wherein said fixation plate is arcuate.

3. The fixation plate of claim 1 further comprising a plurality of said first and second apertures, and said second apertures being arranged in a pattern between said first apertures, wherein said second apertures are centered along the length of the plate.

4. The fixation plate of claim 1 further comprising a plurality of said first and second apertures, wherein said second apertures are arranged along the longitudinal edges of said fixation plate between said first apertures.

5. The fixation plate of claim 1 further comprising a plurality of said first and second apertures and wherein said second apertures are arranged in a staggered pattern along the longitudinal edges of said fixation plate between successive said first apertures.

6. The fixation system of claim 1, wherein the insertion portion of said tack is threaded.

7. A fixation system for fixing the position of a fractured bone, said fixation system comprising:

a plurality of threaded fasteners having a shaft of a first diameter and a head;

an elongated plate having a plurality of first apertures spaced along the length of the plate, said first apertures being arranged and sized to receive said threaded fasteners for fastening the plate to the bone on both sides of the fracture, and a plurality of second apertures spaced along the length of the plate, the second apertures being arranged and sized to receive tacks for temporarily attaching the plate to the bone on both sides of the fracture, said second apertures being smaller than said first apertures; and a plurality of tacks each having an insertion portion, a handle portion and a transition portion, therebetween, said insertion portion having a second diameter smaller than said first diameter of said threaded fasteners, said tacks being so sized that the insertion portions of the tacks may be inserted through respective second apertures and into the bone so that the respective transition portion bears against the plate to temporarily and firmly attach the plate to the bone and said handle portion remaining externally protruding from said fixation plate, so that said tacks can be permanently removed after fastening said fixation plate to the bone by said threaded fasteners.

8. The fixation system of claim 7 wherein the second apertures are arranged in a pattern between successive first apertures centered along the length of the plate.

9. The fixation system of claim 7 wherein the second apertures are arranged along the longitudinal edges of the plate between successive first apertures.

10. The fixation system of claim 7 wherein the second apertures are arranged in a staggered pattern along the fixation plate.

11. The fixation system of claim 7, wherein said threaded fasteners are sized so that the shaft of the threaded fastener may be inserted through a respective first aperture and into the bone so that the head bears against the plate to fasten the plate to the bone.

12. The fixation system of claim 7 wherein the insertion portions of the tacks are threaded.

13. A method of fastening a fixation plate to a fractured bone, comprising the steps of:

positioning a fixation plate against said fractured bone, said fixation plate having a plurality of first apertures adapted to receive threaded fasteners for fastening said fixation plate to said fractured bone, said fixation plate further having a plurality of second apertures adapted to receive tacks for temporarily attaching said fixation plate to said fractured bone;

attaching said fixation plate to said fractured bone by inserting tacks through at least some of said second apertures and into the bone;

fastening said fixation plate to said fractured bone by inserting threaded fasteners through said first apertures and into said fractured bone; and removing said tacks.

14. The method of claim 13, wherein after said attaching step, the method further comprises the steps of:

inspecting the position of said fixation plate against said fractured bone;

removing selected tacks from said fractured bone and said fixation plate;

adjusting the position of said fixation plate and said fractured bone with respect to each other; and inserting tacks into said fractured bone through at least some of said second apertures.

15. The method of claim 14, wherein the tacks inserted into the bone following said adjusting step are inserted into the bone through different second apertures than from which tacks were removed.

16. The method of claim 13, wherein the bone is fractured into at least two bone segments and the step of attaching the plate to the bone includes inserting tacks through second apertures into bone segments on both sides of the fracture.

17. The method of claim 16, wherein after said attaching step the method further comprises the steps of:

inspecting the position of said fixation plate against said fractured bone;

removing selected tacks from at least one segment of said fractured bone and said fixation plate;

adjusting the position of said fixation plate and said one segment of said fractured bone with respect to each other; and inserting tacks into said one segment of said fractured bone through at least one of the second apertures.

18. The method of claim 16 wherein said fracture is a diaphyseal fracture.

19. The method of claim 16 wherein said threaded fasteners comprise heads arranged to bear against said fixation plate to fasten said fixation plate to the bone, and said tacks comprise portions arranged to bear against said fixation plate to temporarily attach the plate to the bone.

20. The method of claim 13, wherein the tacks inserted into the respective bone segment after said adjusting step are inserted into the bone segment through different second apertures than from which tacks were removed.

21. A method of reducing a comminuted bone fracture including a plurality of fractured bone segments, comprising the steps of:

(a) positioning at least one fixation plate against a first bone segment, said fixation plate having a plurality of first apertures adapted to receive threaded fasteners for fastening said fixation plate to said first bone segment, said fixation plate further having a plurality of second apertures adapted to receive tacks for temporarily attaching said fixation plate to said first segment;

(b) attaching said fixation plate to said first bone segment by inserting tacks through at least one of said second apertures and into said bone segment;

(c) positioning a subsequent bone segment to said first bone segment so as to substantially reduce said segments;

(d) attaching said fixation plate to said subsequent bone segment by inserting tacks through at least one of said second apertures and into said subsequent bone segment;

(e) repeating said steps (c) and (d) by positioning a subsequent bone segment to a previous bone segment attached to a fixation plate, and attaching said fixation plate to said subsequent bone segment by inserting at least one tack through at least one of said second apertures and into said subsequent bone segment, until all of said bone segments have been reduced;

(f) fastening said fixation plate to said reduced bone segments by inserting threaded fasteners through said first apertures and into at least some of said bone segments; and (g) removing said tacks.

22. The method of claim 21, wherein after said step (e), the method further comprises the step of:

inspecting the position of said bone segments to confirm substantially satisfactory reduction;

removing selected tacks from said fixation plate and bone segments appearing to have not been satisfactorily reduced;

adjusting the position of bone segments; and inserting tacks into said bone segments through at least some of said second apertures.

23. An elongated substantially rigid fixation plate system for fixing the position of a fractured bone, said fixation plate system comprising:

a plurality of first apertures located along the length of said fixation plate, said first apertures receiving a threaded fastener for fastening the plate to the bone, wherein said threaded fastener has a shaft of a first diameter; and a plurality of second apertures having smaller diameter than said first apertures located along the length of said fixation plate, such that said second apertures removably receive a tack to temporarily and firmly attach said fixation plate to the bone, wherein said tack has an insertion portion of a second diameter smaller than said first diameter of said threaded fastener, and wherein a plurality of said second apertures are disposed in an array centered along the length of said fixation plate.

24. An elongated substantially rigid fixation plate system for fixing the position of a fractured bore, said fixation plate system comprising:

a plurality of first apertures located along the length of said fixation plate, said first apertures receiving a threaded fastener for fastening the plate to the bone, wherein said threaded fastener has a shaft of a first diameter; and a plurality of second apertures smaller than said first aperture located along the length of said fixation plate, such that said second apertures removably receive a tack to temporarily and firmly attach said fixation plate to the bone, wherein said tack has an insertion portion of a second diameter smaller than said first diameter of said threaded fastener, and wherein said second apertures are disposed in a staggered army along the edges of said plate such that a plurality of said second apertures exist along an axis perpendicular to the longitudinal axis of said fixation plate.

* * * * *